United States Patent [19]
Fuller-Pace et al.

[11] Patent Number: 6,020,149
[45] Date of Patent: *Feb. 1, 2000

[54] METHODS OF SCREENING FOR ANTI-MICROBIAL AGENTS AND FOR INHIBITING MICROBIAL GROWTH

[75] Inventors: Frances Victoria Fuller-Pace; David Philip Lane, both of Fife, United Kingdom

[73] Assignee: The University Court of the University of Dundee, Dundee, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/929,738

[22] Filed: Sep. 15, 1997

Related U.S. Application Data

[63] Continuation of application No. 08/530,211, filed as application No. PCT/GB94/00649, Mar. 28, 1994, abandoned.

[30] Foreign Application Priority Data

Mar. 27, 1993 [GB] United Kingdom .................... 9306416
Jan. 27, 1994 [GB] United Kingdom .................... 9401532

[51] Int. Cl.$^7$ ....................................................... C12Q 1/18
[52] U.S. Cl. ................................................. 435/32; 435/21
[58] Field of Search .............................. 435/21, 32, 69.2; 424/9.2

[56] References Cited

U.S. PATENT DOCUMENTS 4,416,995 11/1983 Amaral .................................... 435/291
5,466,576 11/1995 Schulz et al. ............................... 435/6

OTHER PUBLICATIONS

Nature, vol. 337, No. 6203, Jan. 12, 1989, pp. 121–122, P. Linder et al.

Nucleic Acids Research, vol. 18, No. 18, Sep. 25, 1990, pp. 5413–5417, R. Iggo et al, "Identification of a putative RNA helicase in E. coli".

Biological Abstracts, vol. 77, No. 9, 1984, Abstract No. 72366, S. W. Matson et al., DNA–dependent nucleoside 5–triphosphatase activity of gene 4 protein . . .

Chemical Abstracts, vol. 117, No. 19, Nov. 9, 1992, abstract No. 184427, N. R. Bachur et al. "Helicase inhibition by anthracycline anticancer agents".

Biochemistry, vol. 31, No. 10, 1992, pp. 2822–2829, D. Sun et al., "Effect of the (+)–CC–1065–(N3–adenine)DNA adduct on in vitro DNA synthesis mediated by . . . ".

Journal of Biological Chemistry, vol. 258, No. 22, Nov. 25, 1983, pp. 14009–14016, Matson et al, "DNA–dependent Nucleoside 5'–Triphosphatase Activity . . . ".

Molecular Pharmacology, 41:993–998, Dec, 31, 1991, Bachur et al, "Helicase Inhibition by Anthracycline Anticancer Agents".

Journal of Biological Chemistry, vol. 258, No. 22, Nov. 25, 1983, pp. 14017–14024, Matson et al, "The Gene 4 Protein of Bacteriophage T7".

The New Biologist, vol. 3, No. 9, Sep. 1991, pp. 886–895, Kalman et al, "rhlB, A New *Escherichia coli* K–12 Gene with an RNA Helicase–Like Protein Sequence Motif . . . ".

Kalman M., rhlB, A New E. coli K–12 Gene With an RNA Helicase Like Protein Sequence Motif, One of at Least Five Such Possible Genes in a Prokaryote, The New Biologist 3(9) 886–895, Sep. 1991.

Fuller–Pace F., RNA Helicases, Nucleic Acids and Molecular Biology vol. 6 159–173, 1992.

Bachur N., Helicase Inhibition by Anthracycline Anticancer Agents, American Soc for Pharm and Exp Ther vol. 41 993–998, 1992.

*Primary Examiner*—Ralph Gitomer
*Attorney, Agent, or Firm*—Ratner & Prestia

[57] ABSTRACT

A method for determining the anti-microbial activity of a putative anti-microbial agent includes combining a microbially required nucleotide phosphatase, a nucleoside phosphate and the substance to be tested, and assessing the extent of degradation of the nucleoside phosphate in the presence and absence of the substance. The method thus allows the determination of the extent of inhibition of the nucleotide phosphatase by the substance. Preferably the method determines the degree of inhibition of an RNA helicase such as DbpA, which acts selectively on prokaryotic ribosomal RNA. Suitable DbpA inhibitors as well as genetic material encoding for an active form of DbpA are used.

8 Claims, 9 Drawing Sheets

| | |
|---|---|
| eIF-4A | MEPEGVIESNWNEIVDSFDDMN-LSESLLRIYAYGFEKPSAIIQQRAI |
| SrmB | MTVTTFSELE-LDESLLEALQDKGFTRPTAIQAAAI |
| RhlB | MSKTHLTEQKFSDEA-LHPKVVELLEKKGFHNCTPIQALAL |
| RhlD | MAEFETTFADLG-LKAPILEALNDLGYEKPSPIQAECI |
| DbpA | vTAFSTLNVLPPAQLTNLNELGYLTMTPVQAAAL |
| Consensus | *    F***  L   ****L*   G*   ***QA ** |

FIG. 1

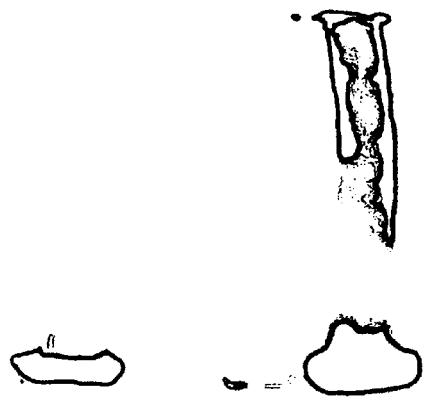
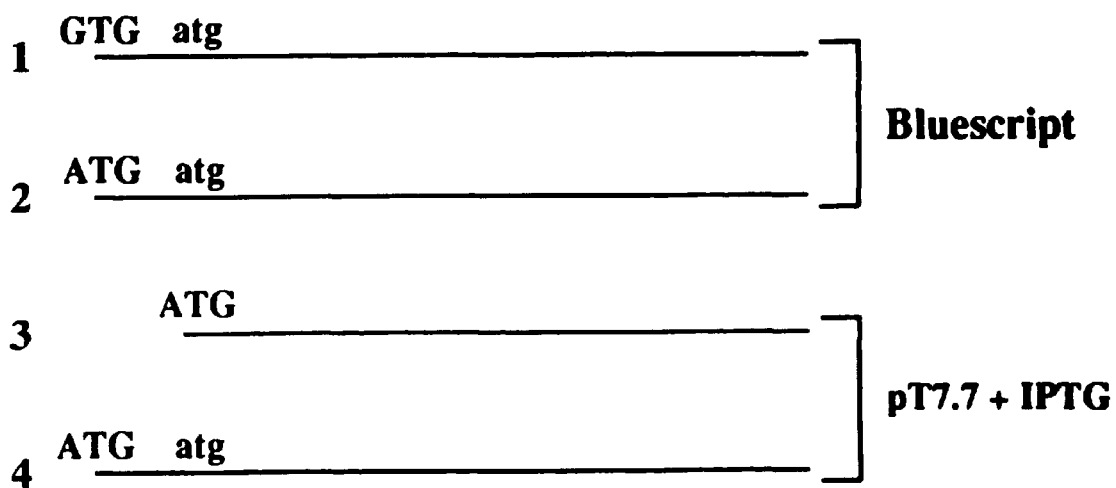
FIG. 2

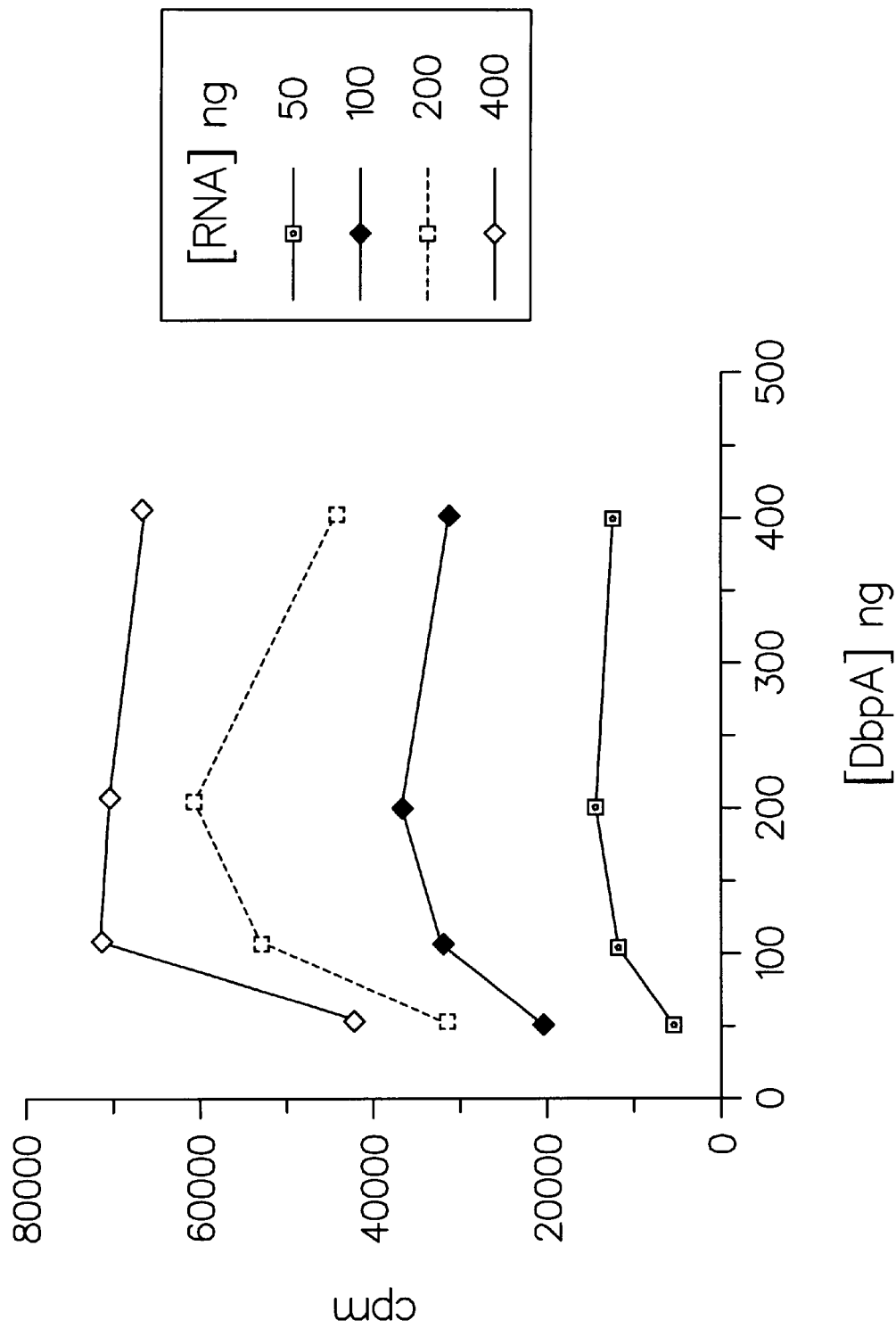

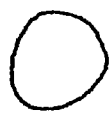 16S + 23S
 16S sense
 16S anti-sense
 23S sense
 23S anti-sense
FIG. 9

METHODS OF SCREENING FOR ANTI-MICROBIAL AGENTS AND FOR INHIBITING MICROBIAL GROWTH

This application is a continuation of application Ser. No. 08/530,211 filed Nov. 20, 1995 now abandoned, which is a 371 of PCT/GB94/00649 filed Mar. 25, 1994.

BACKGROUND OF THE INVENTION

This invention relates to a method for screening anti-microbial agents, to anti-microbial agents identified by the method, and to a method for combatting microbial growth.

More particularly, the method of the invention relates to the use of a putative ribonucleic acid (RNA) helicase to screen for anti-microbial agents.

Ribonucleic acid (RNA) is an essential molecule for cellular viability in both eukaryotic and prokaryotic organisms. The best known form of RNA is messenger RNA (mRNA) which is essential for protein production as it is the means by which genetic information encoded by the genome in the nucleus of a cell is transported into the cytoplasm for translation into protein. However, other types of RNA are also essential for protein production, namely transfer RNA (tRNA) and ribosomal RNA (rRNA). Ribosomes are the site where protein production actually occurs, by the alignment of a specific tRNA molecule (carrying a specific amino acid) with the corresponding codon (base triplet) on the MRNA. Ribosomes are complex molecules and are known to include several polypeptides as well as rRNA. The rRNA is essential for ribosomal function and is highly conserved between different organisms, although there is a distinct difference between the rRNAs of prokaryotic and eukaryotic ribosomes.

In many RNA molecules function depends on not only the actual sequence of nucleic acid bases (the primary structure), but also upon the manner in which the molecule is folded to form a precise three-dimensional shape (the secondary structure).

Manipulation of RNA secondary structure is an essential step in many key processes in the cell, including RNA splicing, ribosome assembly and translation of mRNA into protein. Thus the RNA helicase enzymes which affect RNA secondary structure are essential for the viability of the cell.

Considerable interest in the phenomenon of RNA secondary structure has been generated by the discovery of a large family of proteins with known, or putative, ATP-dependent RNA helicase activity (Linder et al, 1989; Schmid and Linder, 1992; Fuller-Pace & Lane, 1992). Members of this family form part of a larger superfamily of proteins which interact with polynucleotides and nucleotide triphosphates and share seven highly conserved motifs. In several cases these include a characteristic Asp-Glu-Ala-Asp (DEAD) motif which led to their designation as "DEAD box" proteins (Linder, 1989). However as more proteins were assigned to this family both by sequence homology and in some cases biochemical function, it has become clear that there are at least two subgroups: the DEAD and DExH subgroups (Fuller-Pace, 1992).

Individual members of the DEAD box family have been highly conserved throughout evolution (Linder et al, 1989; Iggo, et al., 1991). The dbpA gene was isolated by hybridisation using a probe from the *Saccharomyces pombe* homologue of p68, one of the prototypic DEAD box proteins Iggo, et al, 1990). However analysis of the predicted amino acid sequence showed that, although DbpA contains the conserved motifs characteristic of the DEAD box family, it is in fact no more related to p68 than to any other members of the family. Five such genes have been identified in *E.Coli* (Kalman, et al., 1991). Two of these, srmB (Nishi, et al., 1988) and deaD (Toone, et al., 1991) are thought to be involved in ribosome biogenesis. A third, rhlB, appears to be an essential gene only in some genetic backgrounds (Kalman, et al., 1991) but complementation tests showed no functional complementation between rhlB and srmB, suggesting that these genes have different functions. However little is known about the biological role of rhlB, or rhlE (Kalman, et al., 1991) and dbpA (Iggo, et al., 1990) the other two genes so far identified in *E. coli*.

The only biochemical study reported to date on any of these *E. coli* DEAD box proteins has been for the protein SrmB. This protein was shown to hydrolyse ATP in the presence of nucleic acid but it did not show any specificity requirements. The ATPase activity was induced by Poly(U), Poly(A), tRNA, rRNA and to a lesser extent by single stranded and double stranded DNA (Nishi, et al., 1988). Other DEAD box proteins so far examined biochemically, including the prototypic member of the family, the eukaryotic translation initiation factor eIF-4A (Grifo, et al., 1984) also show similar requirements for RNA which are not specific for any particular RNA species in in vitro ATPase assays.

The highly conserved nature of RNA helicases confirms the importance of their function(s), and therefore they offer an attractive target for the action of anti-microbial therapeutic agents.

However, the identification of such agents has been difficult; although therapeutic agents which inactivate a particular RNA helicase of a microbe infecting a patient are theoretically possible, there is always a risk that the RNA helicase of the patient would also be deactivated by the therapeutic agent, resulting in the disabling of vital processes dependent upon the RNA helicase.

SUMMARY OF THE INVENTION

The surprising finding underlying the present invention is that although purified DbpA exhibits the RNA-dependent ATPase activity characteristic of DEAD box proteins, unlike the other members of the DEAD box family studied to date, DbpA shows a striking dependence on a single specific RNA species for activity, namely the prokaryotic ribosomal RNA known as "23S". The 23S rRNA originally used in these observations was derived from *E. coli*. No activity of DbpA is observed in the presence of eukaryotic ribosomal RNA.

Enzymes which affect RNA, such as DbpA, are essential to produce a functional ribosome by manipulating the secondary structure of the rRNA to the form needed for ribosome activity. It now seems very likely that DbpA acts selectively on the highly conserved 23S rRNA of prokaryotes. Inhibition of DbpA would impede prokaryotic ribosomal function, and since eukaryotic rRNA would not be affected, would provide selective anti-microbial activity.

The finding that DbpA has an absolute requirement for prokaryotic 23S RNA for its ATPase activity means that de-activation of DbpA in a microbe infecting a host will not affect the host cell process, since the DbpA does not affect the host cell RNAs. Thus, the present invention relies upon the substrate specificity of DbpA in a method to test for anti-microbial substances.

In its normal function, DbpA requires the presence of a nucleoside phosphate (generally ATP) before activity to affect RNA structure is observed. In the course of DbpA activity the nucleoside phosphate is degraded. For example where the nucleoside phosphate is ATP, this is converted into ADP and phosphate. The amount of this degradation provides a useful measure of DbpA activity. Thus DbpA and other similar RNA helicases may be regarded as nucleotide phosphatases, or specifically ATPases.

According to the present invention, there is provided a method for determining the anti-microbial activity of a substance, said method comprising:

(i) mixing a microbially-required nucleotide phosphatase, said substance and a nucleoside phosphate; and (ii) evaluating the amount of nucleoside phosphate affected by said phosphatase, and thus the effect of said substance on said phosphatase.

The term "nucleoside" as used herein refers to a molecule consisting only of a base and a sugar. The term "nucleoside phosphate" refers to a nucleoside moiety chemically linked to one or more phosphate groups. Thus, "nucleoside phosphate" includes nucleoside monophosphate (having a single phosphate group), nucleoside diphosphate (having two phosphate groups) and nucleoside triphosphate (having three phosphate groups). The term "nucleotide" is recognised in the art as being equivalent terminology to "nucleoside phosphate" and is used herein to refer to nucleoside molecules having one, two or three phosphate groups as explained above.

The term "nucleotide phosphatase" denotes an enzyme capable of dephosporylating a nucleotide (nucleoside phosphate) molecule either partially or completely. For example, a nucleoside triphosphate may be converted into a nucleoside diphosphate by the nucleotide phosphatase with the concomitant generation of a phosphate moiety, or may be converted to nucleoside monophosphate with the concomitant generation of a pyrophosphate moiety. Likewise a nucleoside diphosphate may be converted into a nucleoside monophosphate or a nucleoside. Under certain conditions an enzyme will operate in the reverse direction so that the nucleoside phosphatase could catalyse the conversion of a nucleoside to a nucleoside phosphate, or add an extra phosphate moiety onto a nucleoside phosphate substrate. Alternative nomenclature for "nucleotide phosphatase" would be "nucleoside phosphate phosphatase".

The microbially-required phosphatase is preferably an ATPase such as an RNA helicase, for example an rRNA helicase. Examples of such phosphatases are mentioned herein, although DbpA is preferred.

The nucleoside phosphate required in the method referred to above may be any such substance which is able to be broken down by the phosphatase. Examples of nucleoside phosphates suitable for the method mentioned above include ATP, deoxy ATP (dATP), ADP, GTP, GDP, AMP, CTP, TTP and the like, or analogues thereof. ATP will normally be used.

Optionally, an agent to stimulate the activity of the nucleotide phosphatase is also provided and is included in the assay at step (i) being added to the nucleotide phosphatase, substance and nucleoside phosphate.

The activity of the nucleotide phosphatase may be RNA dependent and in this case a suitable stimulatory agent is RNA. Preferably, the activity of the nucleotide phosphatase is dependent exclusively upon microbial RNA and most preferably is dependent exclusively upon a distinct species of RNA present in a number of microbes, such as ribosomal RNA or a particular fragment or sequence thereof.

The RNA may be microbial or human, but preferably stimulates degradation of the nucleoside phosphate by the nucleotide phosphatase.

Most preferably, the nucleotide phosphatase and the RNA are selected for the ability of the RNA to stimulate exclusively the nucleotide phosphatase to hydrolyse the nucleoside phosphate.

In one aspect, the present invention provides a method for determining the anti-microbial activity of a substance, said method comprising:

(i) mixing said substance together with an enzyme which affects the secondary structure of prokaryotic rRNA and the essential substrates of said enzyme; and (ii) evaluating the effect of said substance on the activity of said enzyme.

In a preferred aspect the enzyme referred to above is DbpA, the essential substrates of DbpA being prokaryotic 23S RNA or fragments or functional analogues thereof and a nucleoside phosphate, such as ATP, or functional analogues thereof.

Thus, the present invention provides a method for determining the anti-microbial activity of a substance, said method comprising:

(i) mixing said substance together with DbpA, prokaryotic 23S rRNA or a fragment or functional analogue thereof and ATP or a functional analogue thereof; and (ii) evaluating the effect of said substance on the activity of DbpA.

Conveniently, the method will be carried out in vitro.

Preferably, the nucleotide phosphatase is provided in a purified form, for example in substantially pure form.

Preferably, the effect of the substance on the enzyme (or nucleotide phosphatase) is quantified by measuring the amount of phosphate in the reaction mixture. Generally a nucleoside phosphate is degraded to release phosphate and the amount of phosphate released can be measured. Alternatively, phosphate may be incorporated into a nucleoside or nucleoside phosphate so the amount of phosphate take-up (or nucleoside phosphate formed) may be measured. The alteration of the amount of phosphate liberated in the presence of the test substance is preferably compared to the amount liberated in the absence of the substance. The ratio of the two amounts may give an indication of the extent to which the test substance interferes with the activity of the nucleotide phosphatase.

The nucleoside phosphate may include a label such as a radioactive, luminescent, fluorescent or chromophore label, most preferably located on the gamma phosphate moiety of the nucleoside phosphate.

Further according to the present invention, there is provided an anti-microbial agent, which reduces the activity of a microbially required nucleotide phosphatase.

Preferably, where the microbe is a prokaryote, such as *E. coli*, the nucleotide phosphatase is DbpA, although other bacteria and viruses and corresponding enzymes may also be targeted.

Preferably, the agent is an antibiotic although the present invention also encompasses antibodies for use as therapeutic agents.

The anti-microbial agent may be any agent which binds to and/or otherwise reduces the activity of, the nucleotide phosphatase. For example, the anti-microbial agent may comprise an ATP analogue which is not hydrolysable by the nucleotide phosphatase.

Examples of other anti-microbial agents include analogues of the natural substrate of nucleotide phosphatases (eg RNA helicases) or antibodies specific to at least a portion of the enzyme. Any antibody is preferably monoclonally produced.

Further anti-microbial agents comprise non-hydrolysable analogues of nucleoside phosphates or proteins which bind to, and/or reduce the activity of the nucleotide phosphatase.

The mechanism of action of such anti-microbial agents is generally by binding to the nucleoside phosphate binding site on the nucleotide phosphatase, and by preventing or competing with the binding of nucleoside phosphate. Particular anti-microbial agents contemplated are 5'-p-fluorosulfonylbenzoyl-adenosine, adenosine 5'-[B,γ-imido]triphosphate, adenosine 5'-[γ-thio]triphosphate or adenosine 5'-[B,γ-methylene]triphosphate.

The natural substrate of an RNA helicase includes a polynucleotide (such as RNA) and a nucleoside phosphate (such as ATP). Analogues of these substrates are known and may readily be produced by those skilled in the art.

Particularly useful anti-microbial agents include non-functional analogues of microbial 23S rRNA which are still able to bind to the RNA helicase.

The present invention also provides the use of any of the anti-microbial agents defined above to combat microbial growth.

In yet another aspect, the present invention provides a method of combatting microbial growth, said method comprising administering a substance which inhibits a microbially-required nucleotide phosphatase, for example a microbially required RNA helicase, preferably an RNA helicase which acts specifically on prokaryotic rRNA, such as DbpA.

In the course of experimental work leading to the present invention, it was found that an extra N-terminal portion of DbpA may be expressed using a start site further upstream to that putatively identified by Iggo et al supra. The extra N-terminal portion of DbpA has been found by the inventors to be required for activity, and it has also been found that expression of DbpA is enhanced by the use of the upstream start site. Where the extra N-terminal portion of DbpA is present translation from the corresponding genetic material is initiated at a GTG start site upstream of the ATG previously identified as the DbpA start site.

Accordingly, the present invention provides recombinant genetic material encoding for DbpA or parts or functional derivatives thereof, the genetic material including at least part of a sequence naturally upstream from the first ATG in the naturally occurring DbpA gene, or functional equivalents thereof wherein an ATG codon (start site) is present in said upstream sequence.

Preferably all of the sequence naturally upstream (or functional equivalents or derivatives thereof) of the ATG start site up to and including the GTG start site or a functional equivalent therof is included. Desirably the GTG start which is present naturally in the DNA is altered to an ATG codon in the DNA. Incorporation of an ATG codon into the upstream sequence may be achieved by homologous recombination, for example with a chemically synthesised oligonucleotide or by any other known technique. Alternatively an existing codon or nucleotide may be altered or replaced, for example, by site directed mutagenesis. It is also possible for a chemically synthesised version of the upstream sequence to be joined onto the dbpA gene or a part or functional equivalent thereof. Transcription of ATG in DNA will yield AUG in RNA which will then be translated into the relevant amino acid (eg methionine). Similarly GTG in the DNA will be transcribed to GUG in RNA which will be translated accordingly in the protein.

The presence of the upstream sequence has now been found to produce improved activity in the DbpA protein expressed therefrom. Previously, it was not appreciated that inclusion of the upstream sequence had this effect. It is believed that in vivo expression of the dbpA gene occurs from the GTG codon of the upstream sequence. Mutation of this GTG codon to an ATG gives enhanced translation of the higher activity (ie upstream sequence-containing) version of DbpA.

The coding sequence used by Iggo et al supra is shown therein and has been deposited in the EMBL database under accession No X52647. Iggo's dbpA sequence includes a GTG codon 75 to 73 bases upstream of the putative ATG start site identified by Iggo. This GTG codon was altered to ATG by the inventors and the sequence thereby obtained is shown herein as SEQ.ID.NO:2 wherein the ATG produced by alteration is named ATG 1.

SEQ.ID.NO:1 shows the DNA sequence coding for DbpA protein from the modified translation initiation codon ATG 1 to the TAA stop codon at bases 1372–1374.

The sequence of SEQ.ID.NO:2 (which includes SEQ.ID.NO:1 together with flanking sequences therefor) was deposited with the National Collection of Type Cultures (NCTC) at Central Public Health Laboratory, 61 Colindale Avenue London, NW9 5HT, under accession number NCTC 12867 on Mar. 22 1994 as part of a plasmid contained within *E. coli* DH5α.

The term "genetic material" as used herein includes RNA or DNA each in double or single stranded form, and functional equivalents thereof. The genetic material may be produced by any suitable means, including chemical synthesis. "Functional equivalents" means any genetic material which encodes for a polypeptide having the activity required.

Optionally, the genetic material is included as part of a cloning or expression vector. Recombinant vectors including genetic material according to the present invention form a further aspect of this invention. The vectors may include marker elements, origins of replication, or elements to enhance or control expression therefrom, such as promoters and/or enhancers.

Also provided is a method of producing a recombinant vector, said method comprising ligating genetic material according to the present invention to a suitable carrier sequence.

The present invention also provides a transfected host cell, containing genetic material (optionally present as part of a recombinant vector) as defined above.

The present invention also provides a method of producing a transfected host cell, said method comprising transfecting a cell with a vector according to the present invention.

Also provided is a method of producing DbpA, said method comprising expressing DbpA from genetic material according to the invention. Advantageously, the genetic material is present in the form of a vector, and/or in the transfected host cell.

While modifications and improvements may be incorporated without departing from the scope of the invention, the following description illustrates an embodiment of the invention by way of example, with reference to the accompanying drawings.

DESCRIPTION OF THE DRAWINGS

FIG. 1 is a comparison of the amino acid sequences of the amino termini of the *E. coli* DEAD box proteins for which this region is known (Kalman, et al., 1991). The corresponding region for eIF-4A is also shown. Conserved amino acids, as well as conservative substitutions (*) are marked. The first amino acid of DbpA (encoded by GTG) is listed as valine (lower case) but is likely to be methionine, since tRNAfmet will recognise GUG and translate it as methionine (see results).

FIG. 2 shows a Western blot showing DbpA expression in bluescript and pT7.7 plasmids. The plasmids used and the initiation site and codon in each case are indicated and are as follows. 1: bluescript plasmid encoding full length DbpA with a GTG translation initiation codon; 2: bluescript plasmid encoding full length DbpA but with ATG replacing the GTG initiation codon; 3: pT7.7 plasmid in which the 5' end of the gene has been deleted so that the internal ATG acts as the translation initiation codon; 4: pT7.7 plasmid encoding full length DbpA in which the GTG initiation codon has been mutated to ATG to optimise translation initiation in the T7 system. In the case of the pT7.7 plasmids IPTG was added to induce protein expression. DbpA was detected using a DbpA-specific anti-peptide antibody (see "Materials and Methods" below).

FIG. 6 shows ATP hydrolysis by various concentrations of DbpA in the presence of different concentrations of $E.$ $coli$ RNA as indicated. All reactions were allowed to proceed for 1 hour. Released phosphate (cpm-Cerenkov) was measured as described in materials and methods.

FIG. 9 shows an autoradiograph of a PEI thin layer chromatography plate showing the separation (migration from left to right) of radioactive phosphate released from [γ-$_{32}$p]ATP in ATP hydrolysis assays with DbpA in the presence of $E.$ $coli$ 16S and 23S ribosomal RNAs synthesised in vitro as indicated. RNAs were transcribed in vitro as described in materials and methods. In each assay 100 ng of DbpA and 400 ng of RNA were used.

DETAILED DESCRIPTION OF THE INVENTION

Materials and Methods

Figure 3:
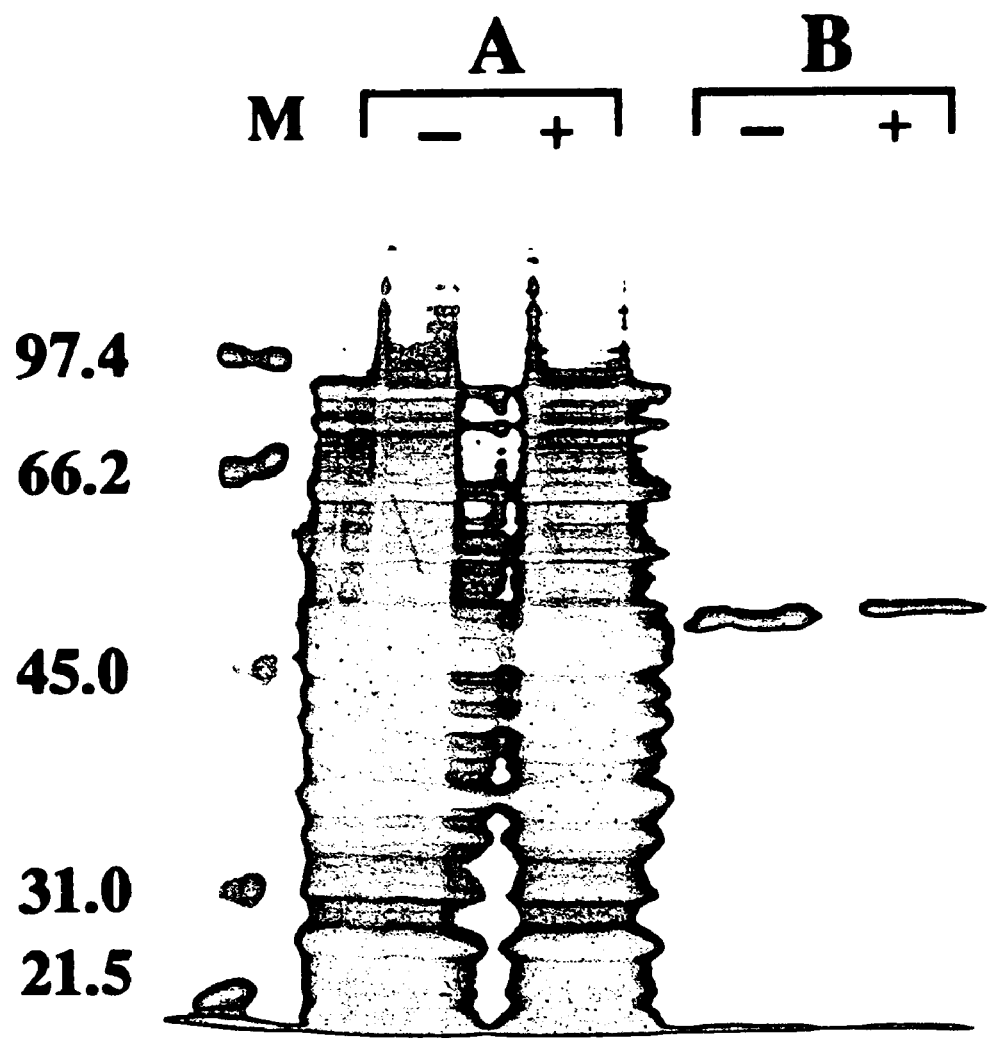
FIG. 3 shows a Coomassie stained SDS polyacrylamide gel showing the proteins in a cell lysate (soluble fraction) from bacteria before (−) and after (+) induction by IPTG. A: bacteria containing the pT7.7 plasmid expressing DbpA where translation initiates at the internal ATG (3 in FIG. 2). B: bacteria containing the pT7.7 plasmid expressing DbpA where translation initiates with ATG at the original GTG position (4 in FIG. 2). The sizes of molecular weight markers (M) are indicated in kilodaltons.

Plasmids and bacterial strains: The bluescript clone encoding DbpA is described by Iggo et al. (Iggo, et al., 1990). The pT7.7 expression vector and the BL21(DE3) cells (Tabor, 1985, Studier, 1990) were a gift from C. A. Midgley. The pKK3535 plasmid encoding the $E.$ $coli$ 16S and 23S rRNAs (Brosius, 1981) was a gift from H. F. Noller and A. Huttenhofer. Preparation of DNA and RNA: This was carried out as described in Sambrook et al. (Sambrook, 1989).

Site directed metagenesis of DbpA was carried out using the Amersham oligodirected metagenesis kit.

Subcloning of the 16S and 23S rRNA and in vitro synthesis of RNA: DNA fragments encoding the 16S and 23S rRNAs respectively were cloned into pGEM3 and pGEM4 in vitro transcription vectors (Promega) so that these RNAs could be synthesised separately. RNA was synthesised using T7 and SP6 polymerases according to Promega instructions.

Growth and induction of bacteria expressing DbpA: A fresh overnight culture of B121(DE3) cells containing the pT7.7 plasmid encoding the dbpA gene under the IPTG inducible 17 promoter (Tabor, 1985) was diluted 30-fold grown to O.D. (650 nm) of 0.3–0.4 at 37° C. and induced by the addition 0.5 mM IPTG. The culture was transferred to 26° C. and grown for a further 4 hours and the cells were harvested by centrifugation. The cell pellet was washed in 50 mM Tris-HCl pH 7.5, harvested by centrifugation and stored at −70° C. until required for DbpA purification.

Separation of Proteins in Bacterial Lysates and Immunoblotting.

Proteins in bacterial lysates (prepared either as described below for soluble protein, or by adding sodium dodecyl sulphate [SDS] buffer directly to bacterial pellets for total protein) were separated by SDS polyacrylamide gel electrophoresis and transferred to nitrocellulose membranes as described in Harlow, 1988. DbpA was detected using an antibody directed against the C-terminal 7 amino acids of DbpA and the Amersham ECL kit.

Purification of DbpA.

The bacterial pellet was resuspended in cold 50 mM Tris-HCl pH 7.5, 10% sucrose, 1 mM Phenyl-methylsulonylfluoride (PMSF), 1 mM Benzamidine, 2 μg/ml Aprotinin, 2 μg/ml Leupeptin (5 ml per litre of bacterial culture) and placed in an ice/salt water bath. NaCl and lysozyme were added to a final concentration of 100 mM and 150 μg/ml respectively and the cells were left in ice/salt water for 30 minutes. They were warmed for 1 minute at 37° C. and returned to ice. This procedure was repeated until the cells were lysed. The suspension was sonicated using an ultrasonic probe to shear the DNA and insoluble material was pelletted by centrifugation (27000G for 15 minutes). The soluble fraction was placed on ice and Polyethylene imine (PEI, Sigma) was added slowly with stirring to a final concentration of 0.2%. A stock 10% PEI solution was prepared from the commercial 50% solution (Sigma) by dialysis as described by Gegenheimer (Gegenheimer, 1990). The precipitated nucleic acid was removed by centrifugation (12000G for 15 minutes) and proteins in the supernate were precipitated by 60% Ammonium sulphate and centrifugation at 27000G for 15 minutes. The protein pellet was resuspended in 50 mM Tris-HCl pH 7.5, 1 mM PMSF, 1 mM Benzamidine, 2 μg/ml Aprotinin, 2 μg/ml Leupeptin (0.5 ml per litre of bacterial culture) and any particulate material was removed by centrifugation at 12000G for 5 minutes. The soluble fraction containing DbpA was further purified on a Pharmacia FPLC Superose 12 column (Trade Mark) in 50 mM Tris-HCl pH 7.5, 50 mM NaCl, 10% glycerol, 1 mM Benzamidine. The DbpA fraction was then purified to homogeneity by binding to single stranded DNA cellulose (Sigma) in 500 mM Tris-HCl pH 7.5, 50 mM NaCl, 1 mM Benzamidine and elution using a 250 mM NaCl step. The pure protein was stored in liquid nitrogen and was found to remain active for several months.

ATP Hydrolysis Assays.

ATPase assays were carried out in 50 mM Tris-HCl pH 7.5, 5 mM MgCl$_2$, 1 mM DTT, 1 µCi [γ-32P]ATP in a final concentration of 0.1 mM ATP. Reactions contained pure DbpA and, unless otherwise stated, a preparation of total *E. coli* RNA in a final volume of 20 µl. The reaction mixtures were incubated at 37° C. for 1 hour, unless otherwise stated. 3 µl of 0.5 M EDTA were added to stop the reaction. ATP hydrolysis was determined by measuring the release of radioactive phosphate; phosphate was separated from residual ATP by thin layer chromatography (TLC). 2 µl aliquots were loaded on a PEI TLC plate (Camlab) and chromatography was carried out in 1M formic acid, 0.5M lithium chloride for 3 hours at ambient temperature. The products were visualised by autoradiography, using Fuji RX film. The phosphate released were obtained by counting the relevant area of the TLC plate (as Cerenkov counts) in a liquid scintillation counter.

One preferred method of assessing the ability of a substance to affect the viability of a microbe utilises the RNA dependent ATPase and putative RNA helicase DbpA which is essential for the normal RNA manipulation functions of a number of bacteria. The method takes advantage of the RNA-dependent ATPase activity of the DbpA. Thus, a preferred RNA-dependent ATP hydrolysis assay for DbpA comprises incubation of DbpA protein in buffer (for example, 500 mM Tris-HCl [pH7.5], 5 mM MgCl$_2$, 1 mM DTT) with bacterial total or ribosomal RNA (rRNA), or a specific RNA substrate (23S rRNA), and 0.1 mM ATP. ATP hydrolysis can be detected by determining the release of radioactive phosphate from [γ-32P] ATP. Free radioactive phosphate can be separated from for example, ATP by chromatography on PEI thin layer chromatography plates in 1M formic acid and 0.5M LiCl, or by any other conventional method. The amount of radioactivity (corresponding to the amount of free phosphate) can then be measured by conventional techniques as described by Sambrook et al. Alternatively, ATP hydrolysis can be measured using a conventional ATP bioluminescent assay. This would allow the semi automated screening of inhibitors using 96-well microtitre plates.

A variety of total RNAs of gram positive and gram negative bacteria from families which include human pathogens have been tested in this assay. These were *Salmonella typhimurium, Shigella flexnerii, Klebsiella pneumoniae, Bordetella bronchoseptica* and *Bacillus subtilis*. All were able to stimulate ATP hydrolysis by *E coli* DbpA.

Examples of anti-microbial agents such as non-hydrolysable analogues are shown in the table below along with the ATPase activity of the nucleotide phosphatase (DbpA) measured in the above assay when the anti-microbial agent was introduced into the reaction mixture. The values of % ATP activity are an average from two assays, compared with a control sample. The anti-microbial agents were added at a 10-fold excess.

TABLE

| Anti-microbial Agents | % ATPase activity |
|---|---|
| 5'-p-Fluorosulfonylbenzoyl-adenosine | 2% |
| Adenosine 5'-[β,γ-imido]triphosphate | 52% |
| Adenodine 5'-[γ-thio]triphosphate | 57% |
| Adenosine 5'-[β,γ-methylene]triphosphate | 90% |

RESULTS

Translation Initiation in dbpA.

Comparison of the predicted amino acid sequence of dbpA with those of other *E. coli* DEAD box genes (Kalman, et al., 1991) showed that the dbpA gene was considerably shorter at the 5' end. However, an upstream in-frame GTG is present in the DNA sequence which, if used as a translation initiation codon, would encode a protein in which the "extra" N-terminal sequence shared several key conserved amino acids (or conservative substitutions) with the other *E. coli* DEAD box proteins (FIG. 1). Translation initiation at a GUG in RNA occurs in about 10% of *E. coli* mRNAs and the initiator tRNAfmet can interact with GUG to give a methionine at the initiation site (Hershey, 1987).] The original dbpA isolate contained upstream sequences (including the putative GTG initiation codon) in a plasmid (bluescript; Stratagene) in which expression of DbpA protein occurred from the authentic *E. coli* promoter. This plasmid did not produce enough protein for direct amino acid sequencing. Therefore, to determine which codon was normally used for translation initiation, two bacterial overexpression plasmids were constructed using the Isopropyl B-D-thiogalactopyranoside (IPTG) inducible pT7.7 system (Tabor, 1985). In one, translation of DbpA initiated at the ATG previously thought to be the authentic initiation codon (Iggo, et al., 1990), while in the other, translation initiated at the upstream GTG. The proteins produced by these plasmids were compared with that produced by the original clone using SDS-polyacrylamide gel electrophoresis. To make the pT7.7 plasmid initiating at the GTG position, this codon was mutated to ATG by oligo-directed mutagenesis to allow optimal translation in the pT7.7 system (see FIG. 2). Thus the two plasmids contained identical ribosome binding sequences and initiation codons.

As shown in FIG. 2, the protein produced by the bluescript clone (lane 1) is of the same size as that produced by the pT7.7 plasmid initiating at the GTG position (lane 4), and no protein of a size corresponding to that initiating at the downstream ATG (lane 3) was observed in the bluescript clone. This indicates that the GTG is the only initiation codon for DbpA when its own promoter and ribosome binding site are used and that the authentic full length DbpA protein includes the sequences upstream from the AUG. The expression of the full-length protein in the pT7.7 plasmid is much higher (20–50 fold; data not shown) than that initiating at the internal AUG. The GTG codon was therefore mutated in the original bluescript clone to ATG (by oligo-directed mutagenesis) to determine if this had any effect on translation efficiency. This mutation virtually abolished expression of DbpA from its natural promoter (FIG. 2, lane 2). This is somewhat surprising since GTG is generally a less efficient translation initiation codon than ATG (Gold, 1988). Interestingly, in in vitro transcription/translation reactions, no difference was observed in the translation efficiency of these two bluescript plasmids (data not shown).

It is not clear why, in the pT7.7 plasmids, the expression of the full length protein initiating at the GTG position is so much higher than that initiating at the internal ATG. Pulse chase analysis of the two proteins showed no obvious difference in their stabilities although the steady state level of the full length protein was inconsistently much higher (data not shown). It was not possible to determine whether there were significant differences in the relative levels of dbpA RNA in the two plasmids by Northern blotting of total RNA preparations from bacterial cells (data not shown). However it is difficult to compare levels of dbpA transcription in the two constructs as the levels of other RNAs in the cells were also apparently different. When the bacterial lysates obtained from the two pT7.7 expression plasmids were compared it was clear that in the plasmid expressing the full-length protein the levels of other proteins in the cell are very low even before IPTG induction (FIG. 3). Moreover a high basal level of DbpA was often obtained (FIG. 3). In large scale preparations however, IPTG produced an increase in the amount of DbpA produced (data not shown).

Purification and ATPase Activity of DbpA.

Figure 4:
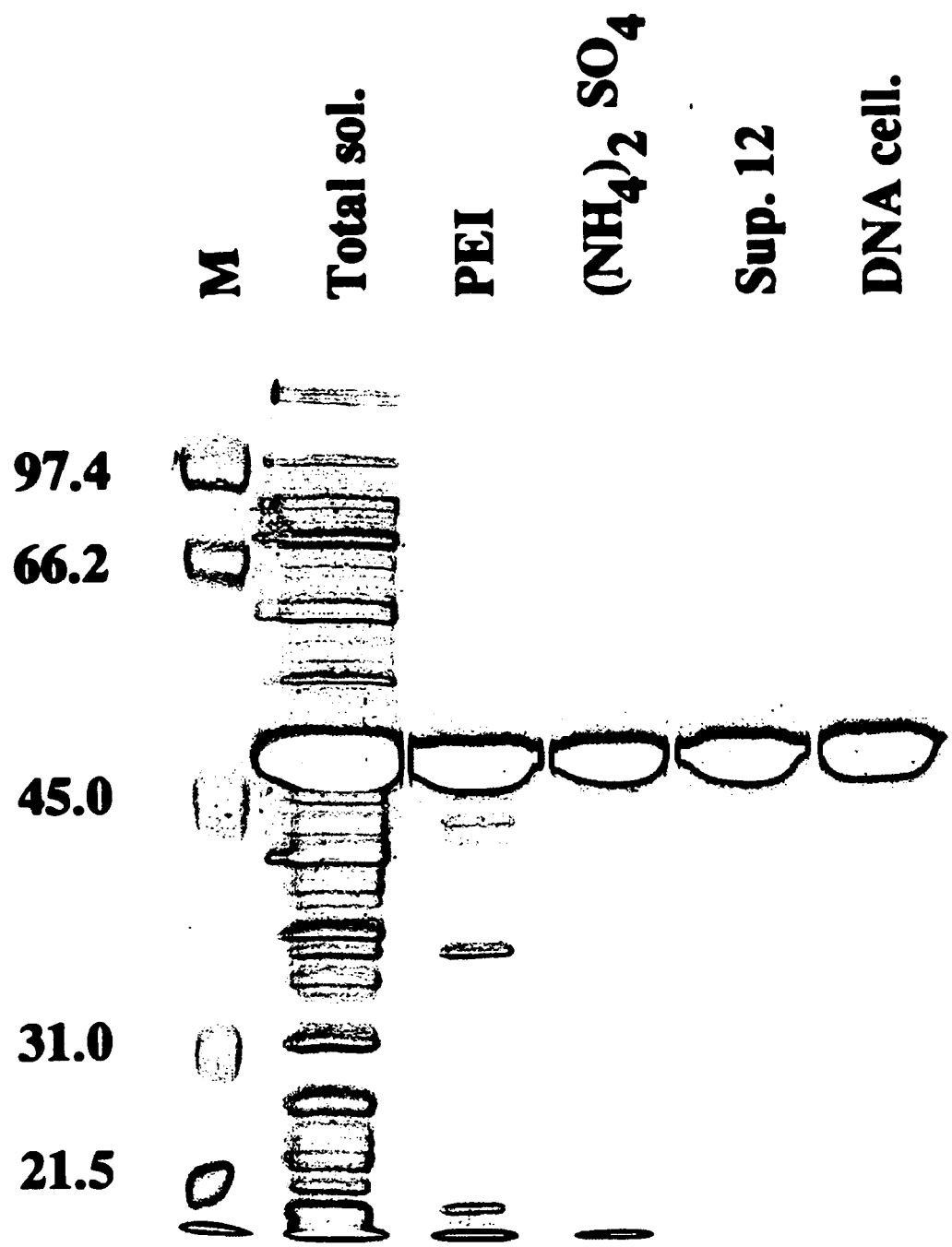
FIG. 4 shows a Coomassie stained SDS polyacrylamide gel showing the purification protocol for DbpA. Total. sol.: total soluble protein in the bacterial lysate. PEI: polyethylene imine. Sup. 12: FPLC superose 12 column. DNA cell.: Single stranded DNA cellulose column. The sizes of molecular weight markers (M) are indicated in kilodaltons.

Unless otherwise stated, the plasmid expressing the complete DbpA gene from the T7 promoter (i.e. initiating at the GTG position) was used for protein production. Cells expressing DbpA were grown and induced with IPTG and the protein was purified to homogeneity as described in materials and methods (FIG. 4). Crude fractions of DbpA contained high concentrations of nucleic acid (both RNA and DNA) which appeared to be bound to the DbpA protein and were not removed by conventional means (eg. high salt concentrations, DNase and RNase). Polyethylene imine (PEI) was therefore used to remove the nucleic acid from the preparation. PEI precipitates nucleic acids and often nucleic acid binding proteins at low salt; the proteins can be subsequently eluted from the pellet by high salt (Gegenheimer, 1990). However with the DbpA crude lysate at 50 mM NaCl, while the nucleic acid was precipitated, most of the DbpA protein remained in solution. Moreover this step provided a substantial purification of DbpA (see FIG. 4). The PEI was removed by precipitating the protein in ammonium sulphate and a highly pure preparation of DbpA was obtained following gel filtration (FPLC Superose 12) and chromatography on single stranded DNA cellulose. This purification protocol routinely produced 2–3 mg of homogeneous DbpA (final yield) per litre of bacterial culture.

Figure 5:
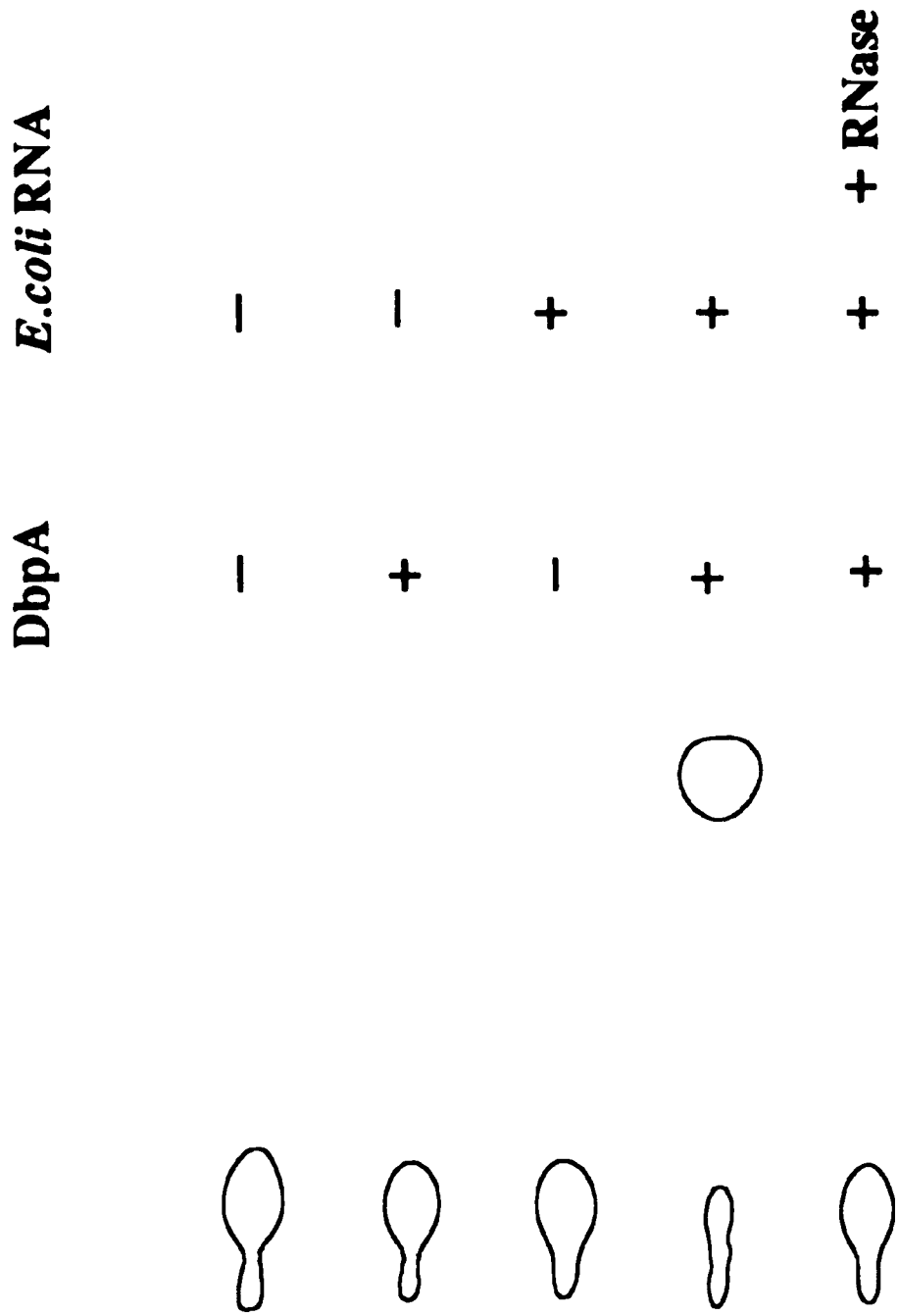
FIG. 5 shows an autoradiograph of a PEI thin layer chromatography plate showing the separation (migration from left to right) of radioactive phosphate released from [γ-32P]ATP in a standard ATP hydrolysis assay. The presence or absence of DbpA and RNA in the reactions is indicated; 200 ng of DbpA and 800 ng of total $E.$ $coli$ RNA were used.

The biochemical function of the pure DbpA was tested by measuring its ability to hydrolyse ATP and determining whether this activity is dependent on the presence of RNA, a function characteristic of members of the DEAD box family of proteins. The ATPase activity of the pure protein was tested by its ability to release radioactive phosphate from [γ-32P] labelled ATP as described in materials and methods. As shown in FIG. 5, DbpA hydrolysed ATP in the presence of total E. coli RNA. No activity was observed in the absence of RNA. Moreover the ATPase activity was abolished when RNase was added to the reaction, indicating that it was dependent on the added RNA. Thus DbpA exhibits the RNA-dependent ATPase activity characteristic of members of the DEAD box family of proteins and like the prototypic members, its activity is not stimulated by single stranded or double stranded DNA.

The $K_m$ for ATP of DbpA was determined to be 150 µM. This value is in the same range reported for eIF-4A, (50, µM) (Grifo, et al., 1984) and p68 (100–1000 µM (Iggo and Lane, 1989).

Assays were to also carried out to determine whether DbpA will hydrolyse other nucleoside triphosphates. Under the conditions used to demonstrate ATP hydrolysis by DbpA, no release of radioactive phosphate was observed with [γ-32P]-labelled GTP (the only other commercially available gamma-labelled nucleotide triphosphate) indicating that this protein will not hydrolyse GTP (data not shown). It was then determined whether other nucleoside triphosphates are hydrolysed by DbpA by investigating whether these would compete with [γ-$_{32}$p]-ATP in standard ATPase assays. In each case a 10-fold excess of the relevant unlabelled nucleoside triphosphate was used in the assay. Competition was only observed with ATP but it has since been shown that deoxy ATP (dATP) is a substrate for DbpA. It remains a possibility that other nucleotide phosphatases within the scope of the invention are able to hydrolyse other nucleoside tri-phosphates.

The biochemical activities of the DbpA protein, in which translation initiated at the internal ATG previously thought to be the authentic initiation codon, were also examined. This protein contains the seven major conserved motifs characteristic of DEAD box proteins (Iggo, et al., 1990; Kalman, et al., 1991; Fuller-Pace, 1992). While this protein was able to bind poly(U) sepharose, ATP agarose and single stranded DNA cellulose in the same way as the full length protein, it was not possible to detect any ATPase activity in pure preparations (data not shown).

Dependence of ATPase Activity on RNA and Protein Concentrations.

Figure 7A:
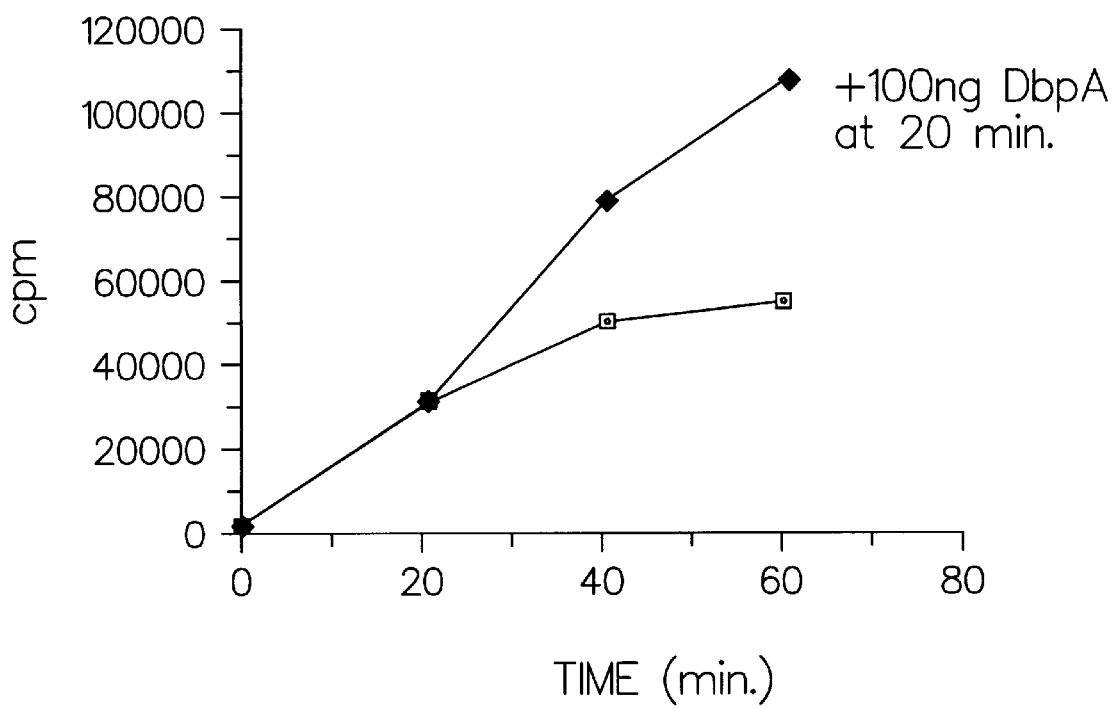
FIG. 7 shows an ATP hydrolysis time course under conditions of limiting RNA (A) and limiting DbpA (B). A: 400 ng DbpA, 100 ng RNA; a further 100 ng of RNA was added after 20 min. B: 100 ng DbpA, 800 ng RNA: a further 100 ng of DbpA was added after 20 min. Released phosphate (cpm-Cerenkov) was measured as described in "Materials and Methods" section. In each case the average counts from two experiments was taken.
Figure 7B:
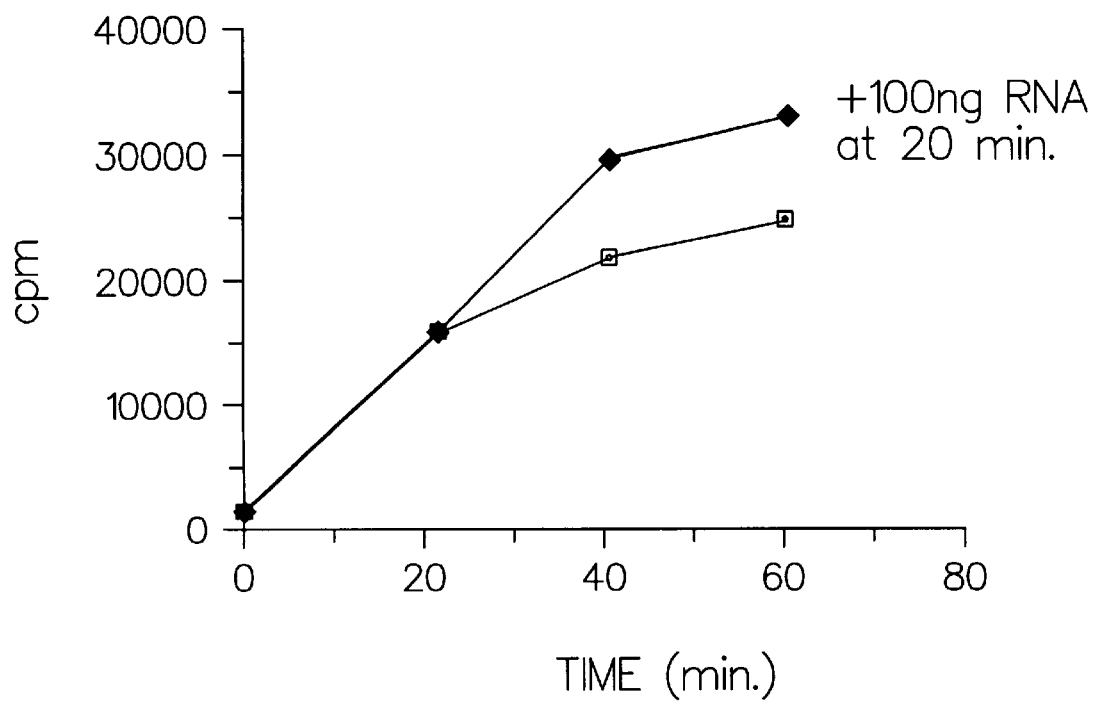

The dependence of ATP hydrolysis by DbpA on total E. coli RNA and DbpA protein concentration was investigated. ATP hydrolysis assays were carried out at increasing protein concentrations in the presence of various RNA concentrations. The incubations were carried out for 1 hour and the release of free phosphate was monitored as described in "Materials and Methods" (FIG. 6). At 50 ng of RNA there was an increase in phosphate release as DbpA concentration increased from 50 to 200 ng. At higher concentrations of DbpA no further increase in product formation was observed, suggesting that the RNA concentration was likely to be limiting. (In each case only a fraction of the ATP was used up in the reaction [data not shown].) As the RNA concentrations were increased up to 400 ng, the amount of phosphate released increased accordingly. However, in each case, a very similar kinetic pattern was observed, i.e. at DbpA concentrations greater than 200 ng no further increase in phosphate release occurred. This again indicated that, although the RNA concentration was being increased, its level was still limiting (FIG. 6). This suggests either that the RNA does not adopt its original conformation after its interaction with DbpA, or that the association of DbpA with the RNA results in the formation of a complex. To distinguish between these two possibilities, two separate parallel experiments were carried out under conditions where either the DbpA or the RNA concentrations were limiting. (determined from FIG. 6). In each experiment the ATP hydrolysis reactions were carried out as a time course with reactions being stopped at times 0, 20, 40, and 60 minutes. After 20 minutes, more of the limiting component (DbpA or RNA) was added to one set of the samples to determine whether this affected the final level of ATP hydrolysis. FIG. 7A confirms that, under conditions of limiting RNA concentration, the addition of more RNA to the reaction stimulates the release of radioactive phosphate from ATP. In FIG. 7B, where the amount of DbpA is limiting, addition of another 100 ng of DbpA during the reaction leads to the release of approximately double the amount of phosphate.

The experiment was repeated using a longer time course (120 minutes) and adding an extra 100 ng DbpA or 500 mg RNA at 80 minutes. The same results were obtained. This is a very striking result. If DbpA were behaving catalytically, the same total amount of phosphate would be released, but the end point would be reached much earlier. However, the observation that increasing the amount of DbpA results in a parallel increase in product formation suggests that DbpA is not released from the reaction to catalyse another round, but remains in a complex with the RNA.

Identification of the Specific RNA Substrate for DbpA.

Figure 8:
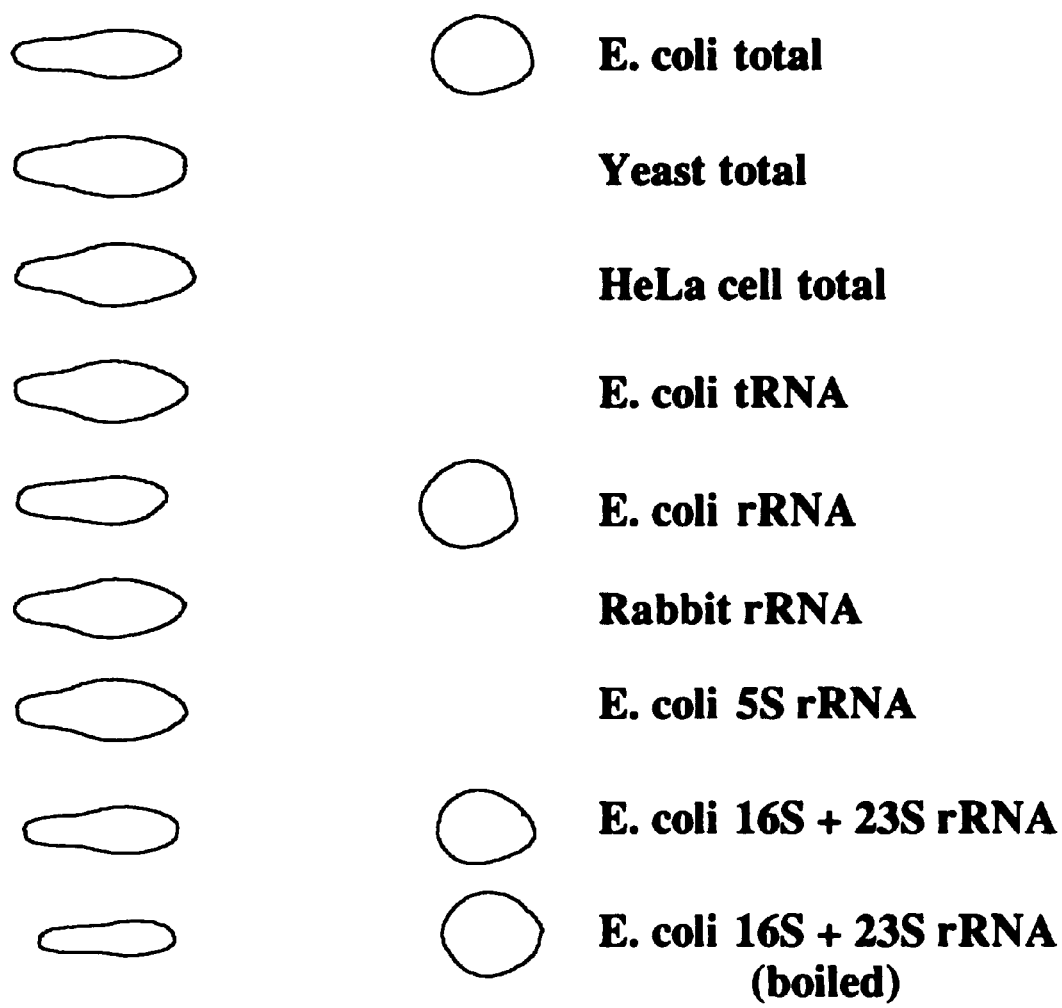
FIG. 8 shows an autoradiograph of a PEI thin layer chromatography plate showing the separation (migration from left to right) of radioactive phosphate released from [γ-32P]ATP in ATP hydrolysis assays with DbpA in the presence of a variety of RNAs as indicated. In each case 200 ng of DbpA and 800 ng of RNA were used.

To determine whether there was any specificity in the requirement for RNA in the ATP hydrolysis reaction a variety of RNA preparations were used. These included total RNA from *E. coli*, yeast and HeLa cells, transfer RNA from *E. coli*, and ribosomal RNA from *E. coli* and rabbit. Strikingly, only the total *E. coli* RNA and the *E. coli* ribosomal RNA stimulated ATPase hydrolysis. No hydrolysis was observed with any of the eukaryotic RNAs or with tRNA (FIG. 8). Similarly, polyu RNA as well as *E. coli* DNA and M13 single stranded DNA did not stimulate ATP hydrolysis (data not shown). This indicated that, unlike the other DEAD box proteins examined biochemically to date, DbpA shows a remarkable degree of specificity in its RNA substrate. For example, the ATPase activities of the eukaryotic translation initiation factor eIF-4A, the *E. coli* SrmB, the yeast splicing factor PRP16, and the plum pox potyvirus CI protein, can be stimulated by several types of RNAs including polyA or polyu (Grifo, et al., 1984; Nishi, et al., 1988; Schwer and Guthne, 1991; Lain, et al., 1991).

To determine whether a particular *E. coli* ribosomal RNA stimulated ATP hydrolysis, 5S and a mixture of 16S and 23S rRNAs which were available commercially (Boehringer) were tested. No activity was observed with 5S rRNA but a mixture of 16S and 23S stimulated ATPase activity (FIG. 8), suggesting that either one, or both, of these RNAs are required to stimulate ATP hydrolysis by DbpA. Interestingly, denaturing the RNA by boiling and rapid cooling on ice did not affect its ability to stimulate ATP hydrolysis by DbpA. This suggests that the sequence/secondary structure recognised by DbpA is stable.

In order to determine whether 16S or 23S, or both, were substrate for DbpA, these RNAs were synthesised separately in vitro and used directly in the ATP hydrolysis reactions. To obtain suitable plasmids for the in vitro synthesis of these RNAs, the genes encoding the 16S and 23S rRNAs were subcloned from the plasmid pKK3535 which contains all the *E. coli* rRNA genes (as the rrn B operon) (Brosius, 1981) into in vitro transcription vectors and the 16S and 23S rRNAs were synthesised separately as described in materials and methods. For both 16S and 23S rRNAs both sense and anti-sense RNAs were synthesised. These RNAs were then used as substrate in the ATP hydrolysis reactions. In these experiments only the 23S sense RNA stimulated ATP hydrolysis; 23S anti-sense and 16S sense and anti-sense RNAs were not substrate for DbpA (FIG. 9). Even with higher concentrations (1 $\mu$g) of RNA, the 16S RNAs and the anti-sense 23S RNA did not stimulate ATP hydrolysis (data not shown). This finding suggests, that in its physiological environment, DbpA interacts specifically with 23S rRNA and that unlike the other DEAD box proteins studied to date DbpA exhibits a remarkable degree of specificity in its requirements for interaction with its RNA substrate.

It has been determined that the specific target for DbpA on 23S rRNA molecule lies within the region between bases 2418–2605. An RNA fragment including this region stimulates full ATPase activity by DbpA.

Discussion

The previously uncharacterised *E. coli* DEAD box protein DbpA has been expressed at high levels and a rapid procedure for the preparation of mg quantities of homogeneous DbpA protein is described herein. Biochemical characterisation of the recombinant DbpA yielded the following significant findings. (1) DbpA hydrolyses ATP in an RNA dependent manner, an activity characteristic of the prototypic members of the DEAD box protein family. (2) ATP hydrolysis assays under conditions where either the RNA or the protein are limiting suggest that a complex is formed between DbpA and its RNA substrate during the ATP hydrolysis reaction. (3) DbpA interacts specifically with prokaryotic 23S rRNA; only this RNA stimulates ATP hydrolysis by DbpA. (4) Although DbpA will bind a variety of RNA species, it will only hydrolyse ATP in the presence of prokaryotic 23S rRNA.

The finding that DbpA shows such specificity in its requirement for RNA in its ATP hydrolysis reaction is particularly interesting. This is the first record of such sequence specificity being shown by a DEAD box protein. None of the other DEAD box proteins, which have been studied biochemically to date, appear to show such specificity requirements in their RNA substrate. For example, the eukaryotic translation initiation factor eIf-4A and the plum pox potyvirus CI protein not only will hydrolyse ATP in the presence of a variety of RNA substrates (including polyu and polyA respectively) (Grifo, et al., 1984; Lain, et al., 1991) but they will also unwind a range of synthetic RNA substrates (Rozen, et al., 1990; Lain, et al., 1990). Unwinding of similar small synthetic RNA molecules was not detected (data not shown). This was perhaps not surprising since DbpA appears to have such specificity in its interaction with RNA to hydrolyse ATP and the substrates used did not stimulate ATP hydrolysis. The size (2904 bases) and the considerable secondary structure of the 23S rRNA molecule (Noller, 1984) makes it difficult to determine whether DbpA will unwind certain specific regions of this RNA using conventional gel shift techniques (Hirling, et al., 1989; Rozen, et al., 1990).

The specificity of the DbpA/23S rRNA interaction may result from a combination of sequence and secondary/tertiary structure, although the finding that boiled RNA is still a suitable substrate suggests that a specific sequence may be the specificity determinant. The identification of the region between bases 2418 and 2685 on the 23S rRNA which stimulates full ATPase activity of DbpA confirms this. Such sequence specificity in a substrate for a DEAD box protein would explain the observation that there are several members of the DEAD box family of proteins even in organisms with relatively small genomes (Linder, 1989). Moreover complementation tests between some of the five DEAD box proteins in *E. coli* showed that these proteins do not complement each other (Kalman, et al., 1991), suggesting that they carry out different functions, presumably acting on different RNA substrates.

23S rRNA, together with the 5S rRNA and 34 ribosomal proteins form the large (50S) subunit of the *E. coli* ribosome. The assembly of the 50S subunit both in vitro and in vivo occurs in three definable stages (Dohme, 1976; Nierhaus, 1982) and the finding that, in vitro, heat is required after half the ribosomal proteins have associated with the RNA suggests that a conformational change is required at this stage. Moreover, while the assembly of ribosomes in vivo takes only a few minutes at 37° C., the two step procedure required for the reconstitution of the 50S subunit in vitro requires very long incubations at high temperatures (Dohme, 1976; Herold and Nierhaus, 1987). It is therefore possible that the conformation of the ribosomal RNAs needs to be subtly modified (perhaps by local unwinding) to allow correct assembly of the ribosomal subunit. In viva this could be carried out by RNA helicases which may be absent in the in vitro reconstitution experiments. There is also some genetic evidence that other DEAD box proteins are involved in ribosome assembly in E. coli. These include the srmB and deaD genes which, when expressed at high levels, suppress temperature sensitive mutations in the genes encoding the ribosomal proteins L24 and S2 respectively (Nishi, et al., 1988; Toone, et al., 1991). Therefore DbpA may be required for correct ribosome assembly. It has now been shown that tRNAs interact with both the 16S and 23S rRNAs (Moazed, et al., 1988; Moazed and Noller, 1989) and that the elongation factors EF-G and EF-Tu interact with a conserved loop in 23S rRNA (Moazed, et al., 1988). These findings highlight the importance of correct conformation of these RNAs within the ribosome for correct translation to take place. Therefore the observation described herein that DbpA, a putative RNA helicase, interacts specifically with 23S rRNA suggests another possible role for this protein, namely in translation. This may have profound implications for the role of DbpA in ribosome structure, assembly, or function.

The observation that 23S rRNA is specifically required to stimulate ATPase activity by DbpA raises an interesting question. DbpA will bind polyu (data not shown) and single stranded DNA. In fact single stranded DNA cellulose was used as a final purification step (see above). This thus indicates a difference between mere binding of DbpA to RNA and specific interaction with its RNA substrate(s) which will result in ATP hydrolysis.

It has been shown herein that in the dbpA gene translation initiation does not occur at the previously predicted AUG (or ATG in DNA) codon (Iggo, et al., 1990), but at an upstream, in-frame GUG (or GTG in DNA). Even in a plasmid construct where the endogenous dbpA promoter and ribosome binding site are used, translation is initiating at the GTG rather than the ATG. Moreover, when the GTG is mutated to ATG in this plasmid, DbpA expression is virtually abolished, suggesting an unusual translation initiation mechanism which requires a GTG initiation codon. GTG is used as an initiation codon in about 10% of E. coli mRNAs (Hershey, 1987).

However it is interesting that when the GTG is mutated to an ATG in a plasmid where the authentic DbpA promoter and ribosome binding site are used, DbpA expression is virtually abolished. (ATG is generally a more efficient translation initiation codon than GTG.) This therefore suggests that for DbpA there appears to be an unusual translation initiation mechanism in which GTG, and not ATG, is recognised as an initiation codon.

In addition, the observation described herein that high level expression of DbpA results in a marked reduction in general translation of other proteins in the cell is provocative and suggests that DbpA may be exerting some general feedback inhibition of translation. The future production of high levels of soluble, homogeneous, stable and enzymatically active DbpA will in future allow detailed analysis of its biochemical function(s) in the cell.

Many antibiotic drugs work by inhibiting protein synthesis in bacteria. However some bacterial strains have appeared which are resistant to these antibiotics. The extreme specificity of DbpA for its RNA substrate and its interaction with 23S rRNA allows the production of novel generations of therapeutic agents such as antibiotics, exploiting this very specific interaction.

Conventional techniques have been described for the production of therapeutic agents such as antibodies and antibiotics. An effective antibiotic may be provided by an analogue of ATP which is not hydrolysable by the particular putative RNA helicase. Thus the RNA helicase would have no energy source and would cease to function. This would be detrimental to the microbe but not to eukaryotic host since the RNA helicase (eg DbpA) would have no effect on, and would not be required for eukaryotic translation.

References

The disclosures in the following papers referred to in this specification are included herein by reference.

Brosius, J, Ullrieh, A, Baker, M A, Gray, A, Dull, T J, Gutell, R R, and Noller, H F (1981).
Plasmid 6, 112–118.
Chang, T H, Arenas, J and Abelson, J (1990).
Proc Natl Acad Sci U S A 87, 1571–5.
Dohme, F and Nierhaus, K H (1976).
J Mol Biol 107, 585–590.
Fuller-Pace, F V and Lane D P.(1992).
In Nucleic Acids and Molecular Biology F Eckstein and D M J Lilley, eds (Berlin: Springer-Verlag), 6, 159–173.
Gegenheimer, P (1990).
Methods Enzymol. 182, 174–193.
Gold, L. (1988).
Ann Rev. Biochem. 57, 199–223.
Grifo, J A, Abramson, R D, Satler, C A and Merrick, W C (1984).
J Biol. Chem. 259, 8648–8654.
Harlow, E and Lane, D (1988). in Antibodies, A Laboratory Manual. (Cold Spring Harbor, New York: Cold Spring Harbor Laboratory).
Herold, M and Nierhaus, K H (1987).
J Biol Chem 262, 8826–33.
Hershey, J W B (1987). In Escherichia coli and Salmonella typhimurium, Cellular and Molecular Biology.
F C Neidhardt, ed.(Washington, DC,American Society of Microbiology).
Hirling, H, Scheffner, M, Restle, T and Stahl, H. (1989).
Nature 339, 562–4.
Iggo, R, Picksley, S, Southgate, J, McPheat J and Lane D P (1990).
Nucleic Acids Res 18, 5413–7.
Iggo, R D, Jamieson, D J 7 MacNeill, S A, Southgate, J, McPheat, J and Lane, D P (1991).
Mol Cell Biol 11, 1326–33.
Iggo, R D and Lane, D P (1989). Embo J.8 1827–31.
Kalman, M, Murphy, H and Cashel, M (1991).
New Biol 3, 886–95.
Lain, S, Martin, M T, Riechmann, J L and Garcia, J A (1991).
J Virol 65, 1–6.
Lain, S, Riechmann, J L and Garcia, J A (1990). Nucleic Acids Res 18, 7003–6.
Linder, P, Lasko, P F, Leroy, P, Melsen, P J, Nishi, K, Schnier, J, Slominski, P P (1989).
Nature 337, 121–122.
Moazed, D and Noller, H F (19S9). Cell 57, 585–97.
Moazed, D, Robertson, J M and Noller, H F (1988).
Nature 334, 362–4.
Nierhaus, K H (1982). Curr. Top. Microbiol. Immunol. 97, 82–155.
Nishi, K, Morel, D F, Hershey, J W, Leighton, T and Schnier, J (1988). [published erratum appears in Nature 1989 Jul 20;340(6230):246]. Nature 336, 496–8.
Noller, H P (1984). Ann. Rev. Biochem. 53, 1 19–162.
Rozen, F, Edery, I, Meerovitch, K, Dever, T E, Merrick, W. C. and Sonenberg, N. (1990). Mol Cell Biol 10, 1134–44.
Sambrook, J, Fritsch, E. F, Maniatis, T (1989).
Molecular Cloning A laboratory Manual Second Edition. Second Edition, (Cold Spring Harbor, New York: Cold Spring Harbor Laboratory)

Schmid, S R and Linder, P (1992).
Mol Microbiol 6, 283–91.
Schwer, B and Guthrie, C (1991). Nature 349, 494–9.
Studier, F W., Rosenberg, A H., Dunn, J J, Dubendorff, J W (1990). Methods Enzymol. 185, 60–89.

Tabor, S and Richardson, C C (1985).
Proc. Natl. Acad. Sci. U. S. A. 82, 1074–1078.
Toone, W M, Rudd, K E and Friesen, J D (1991).
J Bacteriol 173, 3291–3302.

We claim:

1. An in vitro method for quantifying anti-microbial activity of a substance, said method comprising
   (i) incubating a prokaryotic-specific RNA helicase DbpA, said substance and a nucleoside phosphate to form a test mixture, wherein prokaryotic microbial RNA is provided in the mixture as an agent to stimulate activity of said prokaryotic-specific RNA helicase DbpA; and
   (ii) incubating a control mixture comprising said prokaryotic-specific RNA helicase DbpA, said nucleoside phosphate, and said prokaryotic microbial RNA in substantially same concentrations as in the test mixture but without the substance;
   (iii) measuring the amount of nucleoside phosphate degraded in each such mixture; and
   (iv) quantifying antimicrobial activity of the substance by comparing the amount of nucleoside phosphate degraded in the test mixture and control mixture.

2. A method as claimed in claim 1 wherein the microbial RNA is prokaryotic ribosomal RNA.

3. A method as claimed in claim 2 wherein the microbial RNA is prokaryotic 23S ribosomal RNA.

4. A method as claimed in claim 1 wherein the amount of the nucleoside degraded by DbpA is quantified by measuring an alteration in the amount of phosphate in the mixtures.

5. A method as claimed in claim 1 wherein the nucleoside phosphate has a labeled gamma phosphate moiety.

6. A method as claimed in claim 5 wherein the label comprises a radioactive, luminescent or fluorescent label or a chromophore.

7. A method as claimed in claim 1 wherein the microbial RNA is comprised of total cellular RNA.

8. A method as claimed in claim 1 wherein the DbpA is provided in a substantially pure form.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1374 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iii) ANTI-SENSE: NO (vi) ORIGINAL SOURCE:
      (A) ORGANISM: Escherichia coli
      (B) STRAIN: DH5 alpha (ix) FEATURE:
      (A) NAME/KEY: misc_signal
      (B) LOCATION: 1..3
      (D) OTHER INFORMATION: /function= "Altered transcription initiation codon"
          /label= ATG1

(ix) FEATURE:
      (A) NAME/KEY: misc_signal
      (B) LOCATION: 75..77
      (D) OTHER INFORMATION: /function= "Formerly thought to be translation initiation codon"
          /label= ATG2

(xi) SEQUENCE DESCRIPTION: SEQ ID NO: 1:

```
ATGACCGCTT TTTCTACCCT GAATGTTTTG CCTCCCGCCC AACTCACGAA CCTTAATGAG      60

TTGGGTTATT TAACCATGAC GCCGGTGCAG GCCGCCGCGC TTCCGGCGAT CCTTGCCGGA     120

AAAGATGTTC GCGTGCAGGC GAAAACCGGC AGCGGCAAAA CGGCGGCTTT TGGCCTCGGC     180

TTGTTACAGC AAATTGATGC GTCGCTATTT CAAACCCAGG CTTTAGTGCT GTGTCCTACG     240

CGTGAACTGG CGGATCAGGT GGCAGGTGAA TTGCGTCGGC TGGCGCGTTT TCTGCCAAAT     300

ACCAAAATTT TGACGTTGTG CGGTGGTCAA CCGTTCGGTA TGCAGCGTGA TTCGTTGCAA     360

CATGCGCCGC ATATTATCGT GGCAACGCCG GGGCGTTTGC TGGATCACCT GCAAAAAGGC     420

ACGGTATCAC TGGATGCGTT GAATACGCTG GTGATGGATG AGGCCGACCG CATGCTGGAT     480

ATGGGATTTA GCGATGCCAT TGATGATGTC ATCCGTTTTG CGCCTGCATC TCGACAGACG     540

CTTCTGTTTT CGGCAACCTG GCCGGAAGCC ATCGCTGCAA TCAGCGGACG AGTGCAACGC     600

GATCCTTTGG CGATTGAAAT TGACTCAACA GATGCTTTGC CACCCATTGA ACAACAATTT     660

TATGAGACAT CCAGCAAAGG CAAAATTCCT CTGTTGCAAC GGTTATTAAG CTTGCATCAG     720

CCATCCTCTT GCGTGGTGTT TTGCAATACC AAAAAAGATT GCCAGGCTGT CTGCGACGCG     780

CTGAATGAAG TAGGGCAAAG TGCATTGTCA TTACACGGCA ATTTGGAGCA ACGCGATCGC     840

GATCAGACCC TGGTACGTTT TGCTAACGGT AGCGCCCGTG TACTGGTCGC GACTGATGTT     900
```

-continued

```
GCTGCGCGTG GTCTGGATAT TAAATCGCTT GAGCTGGTGG TGAACTTTGA GCTGGCGTGG    960

GACCCTGAAG TTCATGTACA TCGCATCGGT CGTACAGCTC GTGCAGGAAA TAGCGGTCTG   1020

GCGATCAGTT TCTGTGCTCC GGAAGAAGCA CAGCGGGCCA ATATCATTTC TGACATGTTG   1080

CAGATAAAAC TTAACTGGCA AACGCCGCCA GCTAATAGTT CCATTGCGAC GCTGGAAGCA   1140

GAAATGGCAA CGTTGTGTAT CGATGGCGGG AAAAAAGCCA AAATGCGCCC GGGTGATGTA   1200

TTAGGTGCAC TGACAGGAGA TATCGGGCTT GATGGCGCAG ATATTGGCAA AATCGCCGTG   1260

CATCCGGCGC ATGTCTATGT CGCGGTCCGT CAGGCTGTTG CTCATAAAGC ATGGAAACAG   1320

TTACAGGGCG GGAAGATTAA AGGAAAAACG TGCCGGGTGC GGTTATTAAA ATAA         1374
```

(2) INFORMATION FOR SEQ ID NO: 2:

(i) SEQUENCE CHARACTERISTICS:
        (A) LENGTH: 1614 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Escherichia coli
        (B) STRAIN: DH5 alpha (ix) FEATURE:
        (A) NAME/KEY: misc_signal
        (B) LOCATION: 130..132
        (D) OTHER INFORMATION: /function= "Altered translation
            initiation codon"
            /label= ATG1

(ix) FEATURE:
        (A) NAME/KEY: misc_signal
        (B) LOCATION: 205..207
        (D) OTHER INFORMATION: /function= "Formerly thought to be
            translation initiation codon"
            /label= ATG2

(xi) SEQUENCE DESCRIPTION: SEQ ID NO: 2:

```
GATCCCTCGC CCGCAACCCA TGCCTGACCC ACCACCCGAT GAAGAACCGA TTAAATTGTC     60

GCATCGTGAG CGTAGATCTG CGAGGATACG CGCCTGCTAA CTTTGCGTCG ATGACCACGA    120

GAATAGATTA TGACCGCTTT TTCTACCCTG AATGTTTTGC CTCCCGCCCA ACTCACGAAC    180

CTTAATGAGT TGGGTTATTT AACCATGACG CCGGTGCAGG CCGCCGCGCT TCCGGCGATC    240

CTTGCCGGAA AAGATGTTCG CGTGCAGGCG AAAACCGGCA GCGGCAAAAC GGCGGCTTTT    300

GGCCTCGGCT TGTTACAGCA AATTGATGCG TCGCTATTTC AAACCCAGGC TTTAGTGCTG    360

TGTCCTACGC GTGAACTGGC GGATCAGGTG GCAGGTGAAT TGCGTCGGCT GGCGCGTTTT    420

CTGCCAAATA CCAAAATTTT GACGTTGTGC GGTGGTCAAC CGTTCGGTAT GCAGCGTGAT    480

TCGTTGCAAC ATGCGCCGCA TATTATCGTG GCAACGCCGG GGCGTTTGCT GGATCACCTG    540

CAAAAAGGCA CGGTATCACT GGATGCGTTG AATACGCTGG TGATGGATGA GGCCGACCGC    600

ATGCTGGATA TGGGATTTAG CGATGCCATT GATGATGTCA TCCGTTTTGC GCCTGCATCT    660

CGACAGACGC TTCTGTTTTC GGCAACCTGG CCGGAAGCCA TCGCTGCAAT CAGCGGACGA    720

GTGCAACGCG ATCCTTTGGC GATTGAAATT GACTCAACAG ATGCTTTGCC ACCCATTGAA    780

CAACAATTTT ATGAGACATC CAGCAAAGGC AAAATTCCTC TGTTGCAACG GTTATTAAGC    840
```

```
TTGCATCAGC CATCCTCTTG CGTGGTGTTT TGCAATACCA AAAAAGATTG CCAGGCTGTC      900

TGCGACGCGC TGAATGAAGT AGGGCAAAGT GCATTGTCAT TACACGGCGA TTTGGAGCAA      960

CGCGATCGCG ATCAGACCCT GGTACGTTTT GCTAACGGTA GCGCCCGTGT ACTGGTCGCG     1020

ACTGATGTTG CTGCGCGTGG TCTGGATATT AAATCGCTTG AGCTGGTGGT GAACTTTGAG     1080

CTGGCGTGGG ACCCTGAAGT TCATGTACAT CGCATCGGTC GTACAGCTCG TGCAGGAAAT     1140

AGCGGTCTGG CGATCAGTTT CTGTGCTCCG GAAGAAGCAC AGCGGGCCAA TATCATTTCT     1200

GACATGTTGC AGATAAAACT TAACTGGCAA ACGCCGCCAG CTAATAGTTC CATTGCGACG     1260

CTGGAAGCAG AAATGGCAAC GTTGTGTATC GATGGCGGGA AAAAAGCCAA AATGCGCCCG     1320

GGTGATGTAT TAGGTGCACT GACAGGAGAT ATCGGGCTTG ATGGCGCAGA TATTGGCAAA     1380

ATCGCCGTGC ATCCGGCGCA TGTCTATGTC GCGGTCCGTC AGGCTGTTGC TCATAAAGCA     1440

TGGAAACAGT TACAGGGCGG GAAGATTAAA GGAAAAACGT GCCGGGTGCG GTTATTAAAA     1500

TAATGAAATG TTGAATTGCC GGGTGCAAGA GTAAACATCT TATTCGGGAT TGCCGGATGC     1560

GACGCTGGCC GCGTCTTATC CGGCCTCCAT AAGAGTAGCC CGATACGCTT GCGC           1614
```